US008252536B2

(12) United States Patent
Ollikka et al.

(10) Patent No.: US 8,252,536 B2
(45) Date of Patent: *Aug. 28, 2012

(54) INTEGRATED NUCLEIC ACID ANALYSIS

(75) Inventors: Pia Ollikka, Littoinen (FI); Alice Ylikoski, Pikkio (FI)

(73) Assignee: Wallac Oy, Turku (FI)

(*) Notice: Subject to any disclaimer, the term of this patent is extended or adjusted under 35 U.S.C. 154(b) by 0 days.

This patent is subject to a terminal disclaimer.

(21) Appl. No.: 12/832,647

(22) Filed: Jul. 8, 2010

(65) Prior Publication Data
US 2011/0070585 A1    Mar. 24, 2011

Related U.S. Application Data

(63) Continuation of application No. 11/169,010, filed on Jun. 29, 2005, now Pat. No. 7,776,530.

(60) Provisional application No. 60/583,477, filed on Jun. 29, 2004.

(51) Int. Cl.
    C12Q 1/68    (2006.01)
(52) U.S. Cl. ........................................... 435/6.1
(58) Field of Classification Search ................ None
    See application file for complete search history.

(56) References Cited

U.S. PATENT DOCUMENTS

| | | | |
|---|---|---|---|
| 4,683,202 A | 7/1987 | Mullis | |
| 4,786,600 A | 11/1988 | Kramer et al. | |
| 5,118,801 A | 6/1992 | Lizardi et al. | |
| 5,185,243 A | 2/1993 | Ullman et al. | |
| 5,210,015 A * | 5/1993 | Gelfand et al. | 435/6 |
| 5,234,809 A | 8/1993 | Boom et al. | |
| 5,310,652 A | 5/1994 | Gelfand et al. | |
| 5,382,511 A | 1/1995 | Stapleton | |
| 5,399,491 A | 3/1995 | Kacian et al. | |
| 5,409,818 A | 4/1995 | Davey et al. | |
| 5,455,166 A | 10/1995 | Walker | |
| 5,496,562 A | 3/1996 | Burgoyne | |
| 5,501,963 A * | 3/1996 | Burckhardt | 435/91.2 |
| 5,807,527 A | 9/1998 | Burgoyne | |
| 5,856,174 A | 1/1999 | Lipshutz et al. | |
| 5,939,259 A | 8/1999 | Harvey et al. | |
| 5,994,056 A | 11/1999 | Higuchi | |
| 6,103,192 A | 8/2000 | Stapleton et al. | |
| 6,124,120 A | 9/2000 | Lizardi | |
| 6,153,425 A | 11/2000 | Kozwich et al. | |
| 6,168,922 B1 | 1/2001 | Harvey et al. | |
| 6,306,590 B1 | 10/2001 | Mehta et al. | |
| 7,776,530 B2 * | 8/2010 | Ollikka et al. | 435/6 |
| 2002/0012971 A1 | 1/2002 | Mehta | |
| 2003/0143604 A1 | 7/2003 | Storhoff et al. | |

FOREIGN PATENT DOCUMENTS

| | | |
|---|---|---|
| WO | WO 00/12675 | 3/2000 |
| WO | WO 01/92569 A2 | 12/2001 |

OTHER PUBLICATIONS

Henning et al. ("Rapid DNA extraction for molecular epidemiological studies of malaria" Acta Trop. Mar. 15, 1999;72(2):149-55).*

Coyne et al. ("Comparative analysis of the Schleicher and Schuell IsoCode Stix DNA isolation device and the Qiagen QlAamp DNA Mini Kit" J Clin Microbiol. Oct. 2004;42(10):4859-62).*

BD Sprint Advantage® 96 Plate (http://www.clontech.com/clontech/archive/JUL02UPD/pdf/Sprint_96_Plate.pdf; Clonetechniques. Jul. 2002).*

Nurmi et al., "High-Throughput Genetic Analysis Using Time-Resolved Fluorometry and Closed-Tube Detection," Analytical Biochemistry, 2001, vol. 229, pp. 211-217, Elsevier Science, London, England.

Sjöroos et al., "Solid-Phase PCR with Hybridization and Time-resolved Fluorometry for Detection of HLA-B27," Clinical chemistry, 2001, vol. 47, N. 3, pp. 498-504, American Association of Clinical Chemistry, Washington, D.C.

Kline et al., "Polymerase Chain Reaction Amplification of DNA from Aged Blood Stains: QUantitative Evaluation of the "Suitability for Purpose" of Flour Filter Papers as Archival Media," Anal. Chem., 2002, vol. 74, pp. 1863-1869, American Chemical Society, Washington, D.C.

Strizhkov et al., "PCR Amplification on a Microarray of Gel-Immobilized Oligonucleotides: Detection of Bacterial Toxin- and Drug-Resistant Genes and Their Mutations," BioTechniques, Oct. 2000, vol. 29, No. 4, pp. 844-857, Informa Life Sciences Publishing, Westborough, MA.

Caggana et al., "Rapid, Efficient Method for Multiplex Amplification From Filter Paper," Human Mutation, 1998, vol. 11, pp. 404-409, Wiley-Liss, Inc., New York, New York.

Roy et al., "Infrared Fluorescent Detection of D1S80 Alleles from Blood and Body Fluid Collected on IsoCode™ Devices," 1997, Biotechniques, vol. 23, No. 5, pp. 942-945, Informa Life Sciences Publishing Westborough, MA.

Moreira, "Efficient removal of PCR inhibitors using agarose-embedded DNA preparations" Nucleic Acids Res. Jul. 1, 1998;26(13):3309-10.

Henning et al., "Rapid DNA extraction for molecular epidemiological studies of malaria" Acta Trop. Mar. 15, 1999;72(2):149-55.

Coyne et al., "Comparative analysis of the Schleicher and schuell IsoCode Stix DNA isolation device and the Qiagen QlAamp DNA Mini Kit" J Clin Microbiol. Oct. 2004; 42(10):4859-62.

BD Sprint Advantage® 96 Plate (http://www.clontech.com/clontech/archive/JUL02UPD/pdf/Sprint_96_Plate.pdf; Clonetechniques, Jul. 2002.

* cited by examiner

*Primary Examiner* — Christopher M. Babic
(74) *Attorney, Agent, or Firm* — Buchanan Ingersoll & Rooney PC

(57) ABSTRACT

The present invention relates to an integrated method of nucleic acid analysis, and more particularly to a simplified sample pre-treatment, which renders the method more easily automated, where the sample is provided on or applied onto a solid matrix and the subsequent amplification and detection steps are performed in one single, sealed reaction vial without removing the matrix.

27 Claims, 5 Drawing Sheets s
INTEGRATED NUCLEIC ACID ANALYSIS

FIELD OF THE INVENTION

The present invention relates to an integrated method of nucleic acid analysis, and more particularly to a simplified sample pre-treatment, which renders the method more easily automated. The method of the present invention provides minimized risks related to contamination due to minimal handling of the samples.

BACKGROUND OF THE INVENTION

As a result of the rapidly developing genomic testing, whole nucleic acid analysis is an increasing task in many genetic laboratories. The polymerase chain reaction (PCR) is a well established method for amplifying nucleic acid sequences, and the method is routinely used in numerous application areas, such as microbiological testing, expression studies, determination of genetic variation in population, and genetic testing, forensics and food and environmental testing. Testing of nucleic acids using PCR generally involves three steps: sample preparation, amplification and detection. However, the processes for performing the tests used today are often laborious. The current trend is towards simplified assays allowing automation for nucleic acid analysis.

The increased number of tests to be run raises a need for cost-effective operations based on integration and automation of the assay procedures, and the automation of the whole DNA analysis is an increasing task in many genetic laboratories. Although several attempts to perform DNA-analysis as high throughput assays has been described, the logistics of sample handling from sample preparation and pre-treatment to the ultimate analysis still requires manual handling and physical transportation of the samples. In addition, the need to physically transfer amplified DNA samples within the lab poses a serious contamination risk.

One type of a simplified assay that reduces sample handling is provided by so-called closed-tube assays. In closed-tube assays, the FOR product is analyzed in the amplification tube by a homogeneous method, such as TaqMan® (U.S. Pat. No. 5,210,015) or by molecular beacons (U.S. Pat. No. 5,118,801). These approaches allow integration of amplification and detection. However, they lack integration of sample preparation with amplification and detection.

Pre-treatment of the sample is required to remove common inhibitors to nucleic acid amplification that may be present in samples from biological sources. Inhibitors to amplification include, e.g. naturally occurring chelating agents, enzymes and/or proteins that can damage either nucleic acid templates or PCR polymerases used in the amplification reactions. In addition, the common anticoagulants that are used to treat whole blood samples can interfere with nucleic acid amplification reactions.

Numerous technologies have been developed to purify nucleic acids from biological samples but all available procedures are time-consuming and labour intensive. There are several automated stations for sample preparation available on the market, based on silica-chaotrop extraction (U.S. Pat. No. 5,234,809) columns, such as QIAamp®, or the like, and various magnetic bead systems. A different approach is the FTA® Technology (U.S. Pat. No. 5,496,562) that lyses cell membranes as soon as the sample is applied onto a coated filtration matrix allowing immobilization of nucleic acids onto the matrix. After washing, the nucleic acids can be released in a manner that enables them to be amplified by PCR.

Another approach is represented by the development of different solid matrices for collecting, transporting, storing and purifying biological samples, such as clinical whole blood, saliva or faecal samples, for nucleic acid analysis. U.S. Pat. No. 5,807,527 describes a solid medium for long term storage of blood DNA, which comprises a composition, which protects against degradation of DNA, a protein denaturing agent and a free radical trap.

Another example of this approach is the described in U.S. Pat. No. 5,939,259, which discloses an absorbent material, which does not bind nucleic acids irreversibly which is impregnated with a chaotropic salt.

In these known technologies, the DNA of stored blood samples is extracted from the medium before performing PCR, or the DNA is used in PCR in situ on the solid medium after extensive purification, as described in U.S. Pat. No. 5,807,527. Extraction or elution of DNA from the medium requires a multi-step procedure with special solutions and incubations.

Known technologies using solid media for collecting, storing and purifying DNA thus involve multi-step procedures, some using several separate vials and solutions, for generating a sample useful for amplification and detection. Moreover, certain of these methods unnecessarily produce waste.

BRIEF DESCRIPTION OF THE INVENTION

Figure 1:
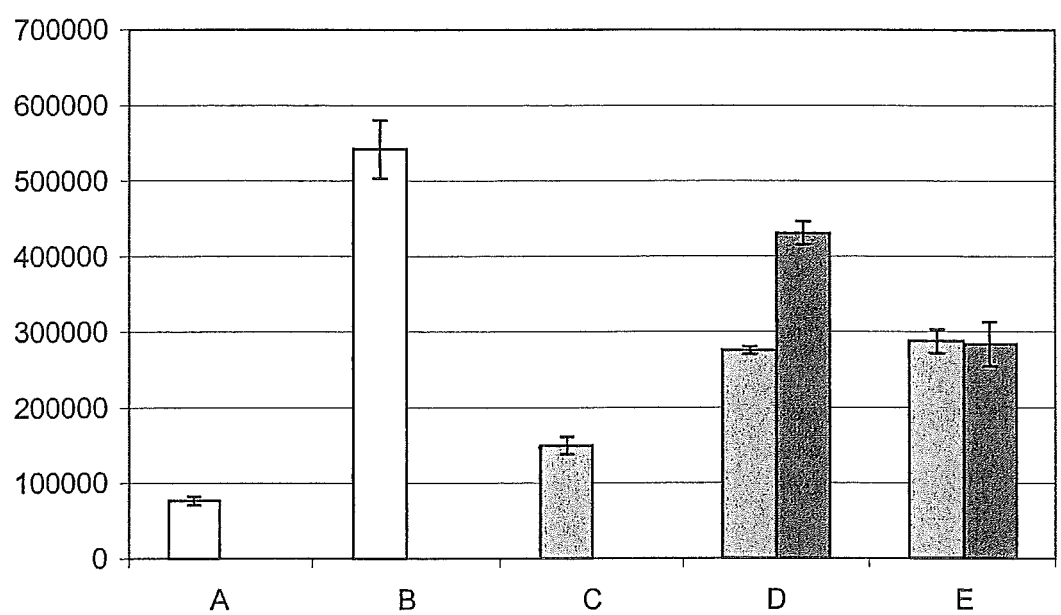
FIG. 1 is a graphical presentation of the result of the comparative test described in Example 1, analyzing the effect of pre-washing dried samples on collection paper.

The present invention relates to a method for analyzing a target nucleic acid in a biological sample, comprising the following steps of i) providing an absorbent matrix in a reaction vial; ii) providing a biological sample containing said target nucleic acids on or applying it onto said absorbent matrix; iii) providing in said reaction vial a reagent mixture for amplifying said nucleic acids; iv) providing in said reaction vial a detection reagent mixture; v) performing an amplification reaction; and vi) detecting the amplified nucleic acids, wherein steps v) and vi) are performed in said vial without removing said matrix from the vial.

More specifically the present invention relates to a method for analyzing a target nucleic acid in a biological sample, wherein the amplification and detection steps are performed in sealed reaction vials without adding or removing any reagents or other components after the amplification step.

The present invention further relates to a method wherein said sample is applied onto the matrix immediately prior to providing the matrix into said reaction vial, without drying and/or storage.

The present invention further relates to a method wherein said matrix is provided in the reaction vial prior to applying the sample directly onto the matrix.

The present invention further relates to a method wherein at least part of said amplification reagents and detection mixtures are provided in dried form prior to the addition of the sample, and said method including an optional further step of adding water prior to performing the amplification step.

DETAILED DESCRIPTION OF THE INVENTION

The present invention provides an integrated method for analyzing nucleic acids contained in a biological sample, comprising a simplified sample pre-treatment, amplification of the target nucleic acid to be analyzed, and detection of said target sequence. Due to the simplified sample pre-treatment, the method allows automation and integration of sample preparation, amplification and analysis of nucleic acids.

The present invention is based on the surprising finding that the amplification and detection steps may be performed on samples collected and, optionally, stored on solid media without prior extraction, washing or elution of the nucleic acids. Only a short incubation to inactive inhibitors and to release the nucleic acids is needed.

Inactivation of inhibitors and denaturation of disturbing proteins is achieved by use of solid matrices based on any porous or absorbing material, e.g. cellulose based filter paper or wadding, cotton wad or fabric, or synthetic plastic material. Suitable matrices for use in the method according to the present invention include absorbent materials which bind proteinaceous material, but do not bind nucleic acids irreversibly, and which are impregnated with e.g., a base, an acid, reducing agents, chaotropic salts, detergents, or other agents to denature natural inhibitors within the sample. Solid matrix material suitable for use in the present invention may be provided as flat sheets, swabs, tablets, pellets or beads, or as a mesh or lattice.

Such solid matrix materials are readily available, and include e.g. the paper matrix provided by Schleicher & Schuell under the trade marks 903™ Specimen Collection paper or IsoCode® for collecting, storing, transporting and purifying DNA.

In a preferred embodiment of the present invention the biological sample is provided on such an absorbent matrix. At least a portion of the matrix containing the sample is transferred to the reaction vial, together with reagents for amplification and detection. The reaction vial is then sealed and moved to a device for performing the amplification reaction. The DNA of the sample is released by a brief heat-treatment. Optionally, if the reagents are not heat stable, e.g. in case of isothermal amplification, the DNA release may be performed at ambient temperature. Surprisingly, after amplification the detection may be performed without opening the reaction vial or removing said matrix.

It has also surprisingly been found, that the sample may be applied onto the matrix immediately prior to use. Thus, in a preferred embodiment of the present invention, the sample is applied onto a suitable solid matrix, whereafter at least a portion of the matrix is transferred to the reaction vial, without prior drying of the matrix. After addition of necessary reagents, the amplification and detection steps are performed.

It has further, surprisingly, been found, that the solid matrix may be provided in the reaction vial and that the sample may be applied directly onto the matrix, and necessary reagents added, once the sample has been applied. Thereafter the amplification and detection steps are performed in the sealed vial.

The term "amplification" is meant to include any method for amplifying nucleic acids known in the art, either thermal cycling methods such as polymerase chain reaction (PCR; U.S. Pat. No. 4,683,202), reverse transcriptase PCR, (U.S. Pat. No. 5,310,652), and ligase chain reaction (LCR; U.S. Pat. No. 5,185,243), and any variations thereof, or isothermal methods, such as Q-Beta replicase technology (U.S. Pat. No. 4,786,600), nucleic acid sequence based amplification (NASBA; U.S. Pat. No. 5,409,818), transcription mediated amplification (TMA; U.S. Pat. No. 5,399,491), strand displacement amplification (SDA; U.S. Pat. No. 5,455,166) and multiple displacement amplification (MDA; U.S. Pat. No. 6,124,120). One preferred method of amplification is asymmetric PCR, described by Innis et al., PNAS 85(24), 1988: 9436-40, which generates single stranded amplification products.

Other known amplification methods may also be useful in the integrated analysis method according to the present invention. The amplification reagents and the amplification procedure may thus vary according to the method of choice.

The detection step is performed by any suitable detection method of choice. Thus the detection reagents may vary according to the method of choice. Suitable detection methods are based on e.g. intercalating reagents to detect the accumulation of amplification product or to perform melting temperature analysis, or labelled primers, or specific primer extension in which directly or indirectly labelled nucleotides are incorporated to the amplification product, or methods in which the directly or indirectly labelled detection probes are degraded during extension, or hybridization with directly or indirectly labelled probes. The detection may be based on e.g. fluorescence resonance energy transfer, fluorescence quenching or environmentally sensitive labels. Suitable detection methods may also include imaging of array of spots or beads by confocal scanning or evanescent wave. The detection step is preferably performed in a closed-tube format without removing the matrix or unreacted components, in order to avoid post-amplification handling.

One preferred detection method is based on hybridization using labelled probes that recognize the amplified target nucleic acids. In such a method, the hybridization, and thus labelling of the target nucleic acids, is achieved simply by lowering the temperature after amplification to hybridization temperature, if necessary, whereafter the unreacted labelled probe is quenched by a complementary probe. Detection of formed labelled hybrids may be performed on the reaction vial, without removing the matrix or other unreacted components. Thus the reaction vials remain unopened after performing the amplification reaction.

In a preferred embodiment of the present invention, the method is further simplified in a way that at least part of the reagents necessary for performing the amplification and detection steps, is provided in the reagent vial in dried form prior to the addition of the sample to be analyzed. Optionally, the absorbent matrix may also be provided in the reaction vial. Such a simplified, integrated assay format minimizes the manual handling, is easily automated and decreases the risk of contamination, as the reaction vials may be sealed immediately after providing the sample and, if necessary, adding water.

A variety of samples can be analyzed using the methods of the invention for preparing a sample for molecular analysis. Such samples include bodily fluids, such as whole blood, saliva, sputum, urine, faecal, peritoneal and pleural fluids; lavations, such as bronchoalveolar, nasal, cervical and intestinal samples; aspiration or biopsy samples; cell cultures or microbial cultures. Specific non-limiting examples include whole blood and saliva samples. The biological samples may also be samples taken from food or environmental samples. In addition to complex biological samples, the method of the present invention is equally suitable for amplifying and analysing pre-treated, purified samples, for example samples where DNA and/or RNA has already been extracted and thereafter stored on matrix.

In a preferred embodiment, the method of the present invention is carried out as follows. The biological sample, such as whole blood, is provided dried on an absorbent matrix sheet or stick, or, optionally, applied to such a matrix by the user, and is allowed to dry onto the matrix. After drying, at least a portion is transferred to the reaction vial. The amplification reagents, comprising primers, nucleotides, polymerase and necessary buffers are added, as well as the detection mixture, comprising directly or indirectly labelled nucleotides or probes, and optionally secondary labels, or intercalators. The vial is then sealed and moved to a thermal cycler. The DNA of the samples is released by a brief heat-treatment. The amplification proceeds after the pre-heating. After amplification, the presence and/or composition of the nucleic acid is detected through the seal on the vial without removing the matrix or even opening the sealed vials at any stage.

In another, highly preferred embodiment, the method of the present invention is carried out as a multi-vial assay. The method is performed using a kit containing dried reagents for amplification and analysis, as well as an absorbent matrix, either as a disk at the bottom of the vials, or as a mesh at least partly filling the vials. The sample to be analyzed is applied, without pre-treatment, directly onto the matrix in the reaction vial. Water is then dispensed into the vials and the vials are sealed and moved to a thermal cycler. The DNA of the samples is released by a brief heat-treatment. The amplification proceeds after the pre-heating. After amplification, the presence and/or composition of the nucleic acid is then detected through the seal of the vials, without removing the matrix. A suitable, readily available format for a kit according to the present invention is e.g. a multi-well plate.

The following examples are given to further illustrate preferred embodiments of the present invention, but are not intended to limit the scope of the invention. It will be obvious to a person skilled in the art that, as the technology advances, the inventive concept can be implemented in various ways. The invention and its embodiments are not limited to the examples de-scribed above but may vary within the scope of the claims.

EXAMPLES

Example 1

Release of Nucleic Acids from Dried Sample Disks

This example shows how the elution of dried blood and saliva disks recommended by manufacturer can be simplified. The recommended pre-wash is omitted and it is shown that the release of nucleic acids can be performed effectively also at room temperature. The release is automated by use of filter plates and automated filtration.

First, whole blood and saliva was collected from a volunteer. The samples were applied onto IsoCode® (Schleicher & Schuell) collection paper and allowed to dry. For analysis, eight 1.5-mm disks were punched and the nucleic acids were eluted according to manufacturer's instructions, i.e. pre-wash with 500 µl of distilled water followed by incubation at +95° C. for 30 min in 135 µl of distilled water. Another eight disks were incubated without pre-wash at +95° C. for 30 min. After incubation, the supernatant was analysed. The automated release was demonstrated by punching a 1.5-mm disk together with 40 µl of distilled water into a vial in a 96-well filtration plate, and the samples were incubated at room temperature for 30 min. After incubation, the filter plate was aligned with reaction plate and the supernatant was transferred into the reaction plate by pressure from top of the filter plate.

The closed-tube PCR amplification and detection reaction was performed in a total volume of 50 µl and the final concentration in the reaction mixture was following: 1×DyNAzyme™ buffer (Finnzymes), 0.2 mM dNTP's, 2.5 mM MgCl2, 0.1 µM CFTR exon 10 forward primer (5' AAG CAC AGT GGA AGA ATT TC 3'; SEQ ID NO:1), 0.1 µM CFTR exon 10 reverse primer (5' CTC TTC TAG TTG GCA TGC T 3'; SEQ ID NO:2), 0.02 U/µl DyNAzyme™ enzyme (Finnzymes), 20 nM analyte specific oligonucleotide probe (5' TAA AGA AAA TAT CAT CTT TGG TGT TTC CTA TAA 3'; SEQ ID NO:3) labelled at its 5' end with a stable fluorescent W14054 Tb chelate (Wallac) and 0.4 µM quencher probe complement to the Tb probe (5' ATG ATA TTT TCT TTA 3'; SEQ ID NO:4) labelled at its 3' with BHQ1 (Biosearch Technologies), 10 µl of supernatant from the 95° C. incubation, and as a control 0.4 ng/µl genomic DNA sample purified from a volunteer's whole blood. The supernatant from the automated release was analysed by adding 10 µl of the reaction mixture to the final concentration described above.

The PCR program was as follows: Pre-heating +95° C. 1 min; 35 cycles of following +95° C. 30 s, ramping from +95° C. to +84 C 0.2° C./s, ramping from +84° C. to +56° C. 2.5° C./s, +56° C. 1 min, +66° C. 1 min and final extension 7 min. After amplification, the reaction was incubated at +30° C. for 5 min, whereafter the time-resolved fluorescence was measured with Victor2 1420 Multilabel Counter (Wallac).

The results of this experiment are shown in FIG. 1 by the average and standard deviation of time-resolved Tb fluorescence of each reaction in duplicates. Negative and positive PCR controls are drawn by bars A and B, respectively. When the simplified release (D and E) is compared to elution by manufacturer's recommendation (C), it is clearly seen that the analysis can be performed with blood (black bars) and saliva (grey bars) disks without pre-wash both at room temperature (D) and at +95 C (E). The result from the supernatants is also comparable to the estimated amount of genomic DNA per blood disk.

Example 2

DNA Analysis from Whole Blood and Saliva

This example shows how the pre-treatment of blood and saliva samples can be simplified to enable simple automation. The sample is collected onto protein denaturing matrix, and the release of nucleic acids from the matrix, amplification and detection are all performed in a single reaction vial. After release, the amplification and detection reagents are added and the reaction vial is sealed, and after amplification and short analytical incubation, the fluorescence is measured without opening the reaction vial, i.e., without removal of the matrix.

First, whole blood and saliva was collected from two volunteers. The samples were applied onto IsoCode® (Schleicher & Schuell) collection paper and allowed to dry. For analysis, a 1.2-mm blood disk or two 1.2-mm saliva disks were punched and the nucleic acids were released at room temperature for 30 min in 40 µl of distilled water. The release was performed in PCR vials and as a reference in separate micro tubes. After release, the PCR/detection reaction mixture was added into the PCR vial comprising the disk. As reference, the 40-µl supernatant from the separate tubes was analysed.

The closed-tube PCR amplification and detection reaction was performed in a total volume of 50 µl. A 10-µl portion of following PCR/detection reaction mixture was added into the PCR: 5×DyNAzyme™ buffer (Finnzymes), 1 mM dNTP's, 12.5 mM MgCl2, 1 µM CFTR exon 10 forward primer (5' AAG CAC AGT GGA AGA ATT TC 3'; SEQ ID NO. 1), 0.25 µM CFTR exon 10 reverse primer (5' CTC TTC TAG TTG GCA TGC T 3'; SEQ ID NO:2), 0.1 U/µl DyNAzyme™ enzyme (Finnzymes), 83 nM analyte specific oligonucleotide probe (5' ACC AAA GATGAT ATT TAA A 3'; SEQ ID NO: 5) labelled at its 5' end with a stable fluorescent W8184 Eu chelate (Wallac) and 166 nM quencher probe complement to the Eu probe (5' TCA TTG GTG TTT 3'; SEQ ID NO:6) labelled at its 3' with BHQ1 (Biosearch Technologies). As a control, 20 ng/reaction of genomic DNA sample purified from a volunteer's whole blood was analysed.

The PCR program was as follows: Pre-heating 95° C. 1 min; 35 cycles of following +95° C. 30 s, +56° C. 1 min, +66° C. 1 min, final extension 7 min and final denaturation 8 min. After amplification, the reaction was incubated at +40° C. for 20 min and at +22° C. for 15 min, whereafter the time-resolved fluorescence was measured with Victor2 1420 Multilabel Counter (Wallac) directly from the unopened vial.

Figure 2:
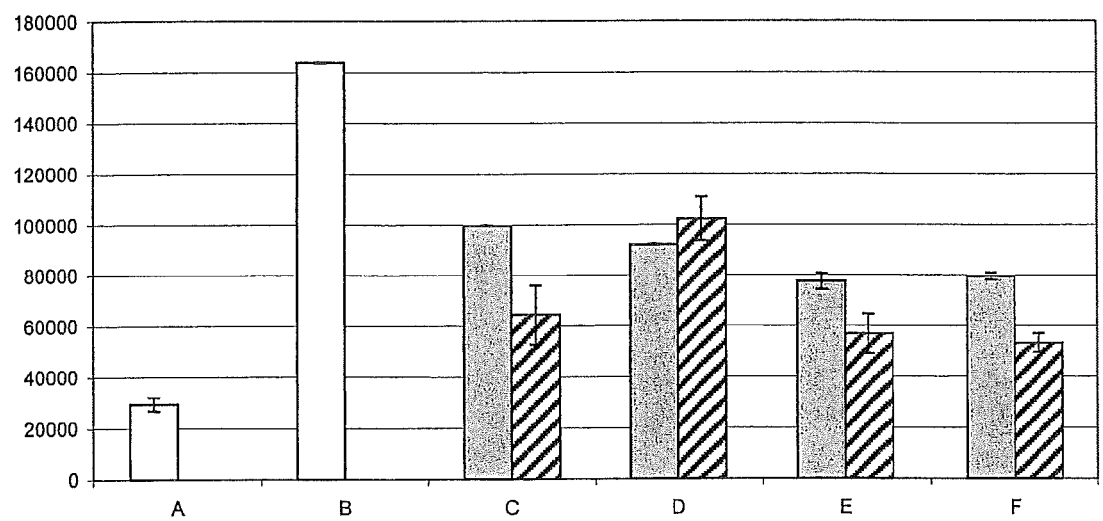
FIG. 2 is a graphical presentation of the result of the test described in Example 2, where the release of DNA from dried samples, amplification and detection of amplified DNA is performed in a single reaction vial.

The results of this experiment are shown in FIG. 2 by the average and standard deviation of time-resolved Eu fluorescence of each reaction in triplicates. Negative and positive PCR controls are drawn by bars A and B, respectively. C-D represent results from blood and E-F from saliva samples obtained from 2 volunteers. When the integrated release in the reaction vial without removal of matrix at any point (hatched bars) is compared to release in a separate vial (grey bars), it is clearly seen that the whole analysis can be performed with blood disk and saliva disks without removal of disk. The result shows that the release from the matrix can be performed at room temperature in the reaction vial and after amplification the detection can be performed without removal of matrix enabling simple automation of whole analysis.

Example 3

Integrated DNA Analysis from Whole Blood and Saliva

This example shows how the release of nucleic acids from matrix can be further simplified to enable simple automation. The sample is collected onto protein denaturing matrix, and the release of nucleic acids, amplification and detection are all performed in a single reaction vial even in the presence of amplification and detection reagents. The matrix comprising the sample is added together with the amplification/detection reagents into a reaction vial, the vial is sealed, and after amplification and short analytical incubation, the fluorescence is measured without opening the reaction vial, i.e. without removal of the matrix.

First, whole blood and saliva was collected from two volunteers. The samples were applied onto IsoCode® (Schleicher & Schuell) collection paper and allowed to dry.

For analysis, a 1.2-mm blood disk or two 1.2-mm saliva disks were punched into PCR vials. The closed-tube PCR amplification and detection reaction was performed in a total volume of 50 µl in following PCR/detection reaction mixture: 1×HotStarTaq® buffer (Qiagen), 0.2 mM dNTP's, 2.5 mM MgCl2, 0.05% BSA, 0.2 µM CFTR exon 10 forward primer (5' AAG CAC AGT GGA AGA ATT TC 3'; SEQ ID NO:1), 0.05 µM CFTR exon 10 reverse primer (5' CTC TTC TAG TTG GCA TGC T 3'; SEQ ID NO:2), 0.02 U/µl DyNAzyme™ enzyme (Finnzymes), 17 nM analyte specific oligonucleotide probe (5' ACC AAA GAT GAT ATT TAA A 3'; SEQ ID NO:5) labelled at its 5' end with a stable fluorescent W8184 Eu chelate (Wallac) and 33 nM quencher probe complement to the Eu probe (5' TCA TTG GTG TTT 3'; SEQ ID NO:6) labelled at its 3' with BHQ1 (Biosearch Technologies). As a control, 20 ng/reaction of a volunteer's genomic DNA sample on disk was analysed. As a reference, the release of nucleic acids was performed at room temperature for 30 min in 40 µl of distilled water, and analysed in the closed-tube PCR/detection after addition of a 10-µl portion of reaction mixture as 5×concentrate.

The PCR program was as follows: Pre-heating +95° C. 15 min; 35 cycles of following +95° C. 30 s, +56° C. 1 min, +66° C. 1 min, final extension 7 min and final denaturation 8 min. After amplification, the reaction was incubated at +40° C. for 20 min and at +22° C. for 15 min, whereafter the time-resolved fluorescence was measured with Victor2 1420 Multilabel Counter (Wallac).

Figure 3:
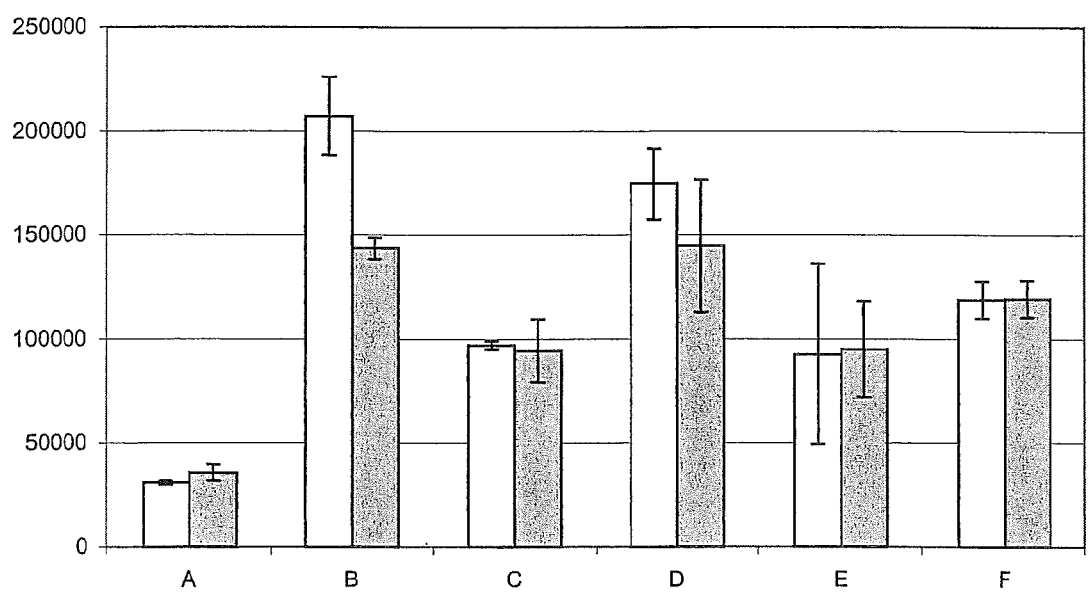
FIG. 3 is a graphical presentation of the result of the test described in Example 3, where the release of DNA from dried samples, amplification and detection of amplified DNA is performed in a single reaction vial, and where all necessary reagents were added simultaneously.

The results of this experiment are shown in FIG. 3 by the average and standard deviation of time-resolved Eu fluorescence of each reaction in triplicates. Negative and positive PCR controls are drawn by bars A and B, respectively. C-D represent results from blood and E-F from saliva samples obtained from 2 volunteers. When the release in amplification/detection reagents (grey bars) is compared to release in distilled water (white bars), the result is nearly equal with both methods. The result shows that release from the matrix can be performed even in the amplification/detection mixture, and the whole process can be performed in a single vial in a closed-tube format enabling simple automation of whole analysis.

Example 4

Integrated Sample Pre-Treatment and DNA Analysis from Whole Blood

This example shows how the matrix comprising the sample can be used in analysis right after the application of the sample enabling development of amplification/detection devices comprising the matrix in the reaction vial. The sample is applied onto the protein denaturing absorbent matrix in the reaction vial, the amplification/detection reagents are added, the vial is sealed, and after amplification and short analytical incubation, the fluorescence is measured without opening the reaction vial.

The closed-tube PCR amplification and detection reaction was performed in a total volume of 50 µl. First, a 1.2-mm disk from IsoCode® (Schleicher & Schuell) collection paper was punched into PCR vials. Then, a 0.35-µl sample from a volunteer's whole blood was applied into the vial. After various time points, a 50-µl portion of PCR/detection reaction mixture (as follows) was added: 1×Phusion™ HF buffer (Finnzymes), 0.2 mM dNTP's, 2.5 mM MgCl2, 0.02% BSA, 0.2 µM CFTR exon 10 forward primer (5' AAG CAC AGT GGA AGA ATT TC 3'; SEQ ID NO:1), 0.05 µM CFTR exon 10 reverse primer (5' CTC TTC TAG TTG GCA TGC T 3';

SEQ ID NO:2), 0.02 U/μl DyNAzyme™ enzyme (Finnzymes), 17 nM analyte specific oligonucleotide probe (5' ACC AAA GAT GAT ATT TAA A 3'; SEQ ID NO:5) labelled at its 5' end with a stable fluorescent W8184 Eu chelate (Wallac) and 33 nM quencher probe complement to the Eu probe (5' TCA TTG GTG TTT 3'; SEQ ID NO:6) labelled at its 3' with BHQ1 (Biosearch Technologies). As a control, 20 ng/reaction of a volunteer's genomic DNA sample on disk was analysed.

The PCR program was as follows: Pre-heating +95 C 15 min; 35 cycles of following +95° C. 30 s, +56° C. 1 min, +66° C. 1 min, final ex-tension 7 min and final denaturation 8 min. After amplification, the reaction was incubated at +40° C. for 20 min and at +22° C. for 15 min, whereafter the time-resolved fluorescence was measured with Victor2 1420 Multilabel Counter (Wallac).

Figure 4:
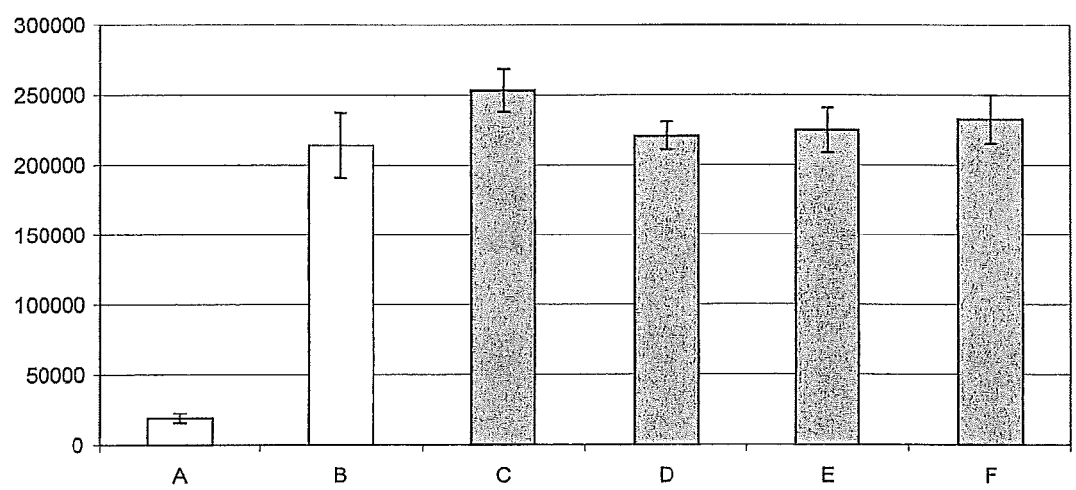
FIG. 4 is a graphical presentation of the result of the test described in Example 4, where a whole blood sample is applied to an absorbent matrix in the reaction vial, and amplification and detection of amplified DNA is performed in the same reaction vial.

The results of this experiment are shown in FIG. 4 by the average and standard deviation of time-resolved Eu fluorescence of each reaction in 4 replicates. Negative and positive PCR controls are drawn by bars A and B, respectively. C-F represent results from blood samples analysed. The signal from the analysis which has been performed right after applying the sample into the amplification/detection vial comprising the matrix (F) is equal to those which have been let dry 1, 2 and 16 h (C-E, respectively). The result shows that the whole process can be performed in a single vial avoiding multiple steps from sample pre-treatment to detection allowing very simple automation.

Example 5

Integrated DNA Analysis from Whole Blood Using Dried Reagents

This example shows the extreme simplification of the nucleic acid analysis process from sample pre-treatment to detection. The reagents are dried into the reaction vial, and the sample is either applied onto the protein denaturing absorbent matrix in the vial, or the matrix containing sample is punched into the vial together with water. Then the vial is sealed, and after amplification and short analytical incubation, the fluorescence is measured without opening the vial.

First, a 12.5 μl portion of following amplification/detection reaction mixture was allowed to dry in the reaction vial at room temperature for 2 h: 4×Phusion™ HF buffer (Finnzymes), 0.8 mM dNTP's, 10 mM MgCl2, 0.08 BSA, 0.8 μM CFTR exon 10 forward primer (5' AAG CAC AGT GGA AGA ATT TC 3'; SEQ ID NO:1), 0.2 μM CFTR exon 10 reverse primer (5' CTC TTC TAG TTG GCA TGC T 3'; SEQ ID NO:2), 0.08 U/μl DyNAzyme™ enzyme (Finnzymes), 66 nM analyte specific oligonucleotide probe (5' ACC AAA GAT GAT ATT TAA A 3'; SEQ ID NO:5) labelled at its 5' end with a stable fluorescent W8184 Eu chelate (Wallac) and 133 nM quencher probe complement to the Eu probe (5' TCA TTG GTG TTT 3'; SEQ ID NO:6) labelled at its 3' with BHQ1 (Biosearch Technologies).

Then, the reaction vial comprising the dried reagents was used in the closed-tube PCR amplification and detection reaction in a total volume of 50 μl. A 1.2-mm blood disk of previously collected volunteer's sample on IsoCode® (Schleicher & Schuell) was punched into the reaction vial with simultaneous dispensing of 50 μl of distilled water. Or, a 1.2-mm disk from IsoCode® (Schleicher & Schuell) collection paper was punched into the vial, and then, a 0.35-μl sample from a volunteer's whole blood was applied into the vial, and 50 μl of distilled water was added. Also, supernatant after release of nucleic acids in 50 μl of distilled water in a separate vial at room temperature for 30 min was used as sample in analysis. As a positive control, 20 ng/reaction of a volunteer's genomic DNA sample on disk was analysed.

The PCR program was as follows: Pre-heating +95° C. 15 min; 35 cycles of following +95° C. 30 s, +56° C. 1 min, +66 C 1 min, final ex-tension 7 min and final denaturation 8 min. After amplification, the reaction was incubated at +40° C. for 20 min and at +22° C. for 15 min, whereafter the time-resolved fluorescence was measured with Victor2 1420 Multilabel Counter (Wallac).

Figure 5:
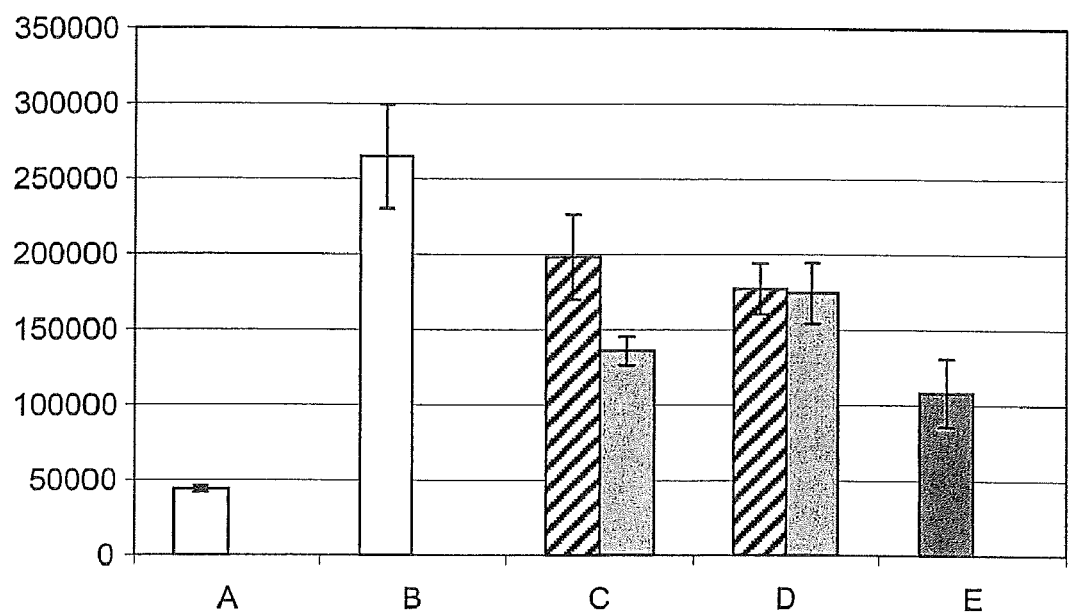
FIG. 5 is a graphical presentation of the result of the test described in Example 5, where all necessary reagents were provided in dried form in the reaction vial.

The results of this experiment are shown in FIG. 5 by the average and standard deviation of time-resolved Eu fluorescence of each reaction in 4 replicates. Negative and positive PCR controls are drawn by bars A and B, respectively. C-E represent the results from blood samples obtained from 3 volunteers, respectively. When the integrated release in the reaction vial (hatched bars) is compared to the release in a separate vial (grey bars), it is clearly seen that the whole analysis can be performed using dried reagents even without removal of disk. Also, E shows that the matrix can be integrated into the reaction vial comprising the dried reagents, and the sample can be applied right before the analysis. The result shows that the whole process from sample pre-treatment to detection can be performed in a single reaction vial comprising all reagents dried enabling extremely simple automation.

The invention claimed is:

1. A method for analyzing a target nucleic acid in a biological sample, comprising the following steps:
   a) providing a reaction vial consisting of a single compartment and a closable lid, wherein said reaction vial contains:
      i) an absorbent matrix;
      ii) a biological sample on said absorbent matrix, wherein said biological sample comprises said target nucleic acid, and wherein said nucleic acid has not been extracted, washed, and/or eluted from said biological sample;
      iii) a reagent mixture for amplifying said nucleic acid;
      iv) a reagent mixture for detecting the amplified nucleic acid, and
   b) closing the lid of said reaction vial;
   c) releasing said nucleic acid from said absorbent matrix;
   d) amplifying said nucleic acid; and
   e) detecting the amplified nucleic acid through the use of a labelled probe as a result of fluorescence resonance energy transfer; wherein:
   steps c) through e) are performed in said reaction vial without removing said absorbent matrix from said reaction vial and without opening said reaction vial.

2. The method according to claim 1, wherein said biological material is applied to said absorbent matrix prior to transferring said absorbent matrix and said biological sample to said reaction vial.

3. The method according to claim 2, wherein said biological sample is applied to said absorbent matrix immediately prior to transferring said absorbent matrix and said biological sample to said reaction vial, without drying or storage.

4. The method according to claim 1, wherein said absorbent matrix is transferred to said reaction vial prior to application of said biological sample to said absorbent matrix.

5. The method according to claim 1, wherein said absorbent matrix comprises an absorbent material that does not irreversibly bind nucleic acids.

6. The method according to claim 5, wherein said absorbent matrix comprises one or more of a protein binding agent and a protein denaturing agent.

7. The method according to claim 5, wherein said absorbent matrix comprises a chaotropic agent.

8. The method according to claim 1, wherein in step (a) at least part of said reagent mixture for amplifying nucleic acids and said reagent mixture for detecting amplified nucleic acids are contained in said reaction vial in dried form.

9. The method according to claim 1, wherein step d) is performed by polymerase chain reaction (PCR).

10. The method according to claim 1, wherein step e) is performed by hybridizing said amplified nucleic acid to a fluorescently labelled probe.

11. The method according to claim 8, further comprising adding water to said reaction vial prior to step b).

12. The method according to claim 1, wherein said target nucleic acid is DNA.

13. The method according to claim 1, wherein said target nucleic acid is RNA.

14. A method for analyzing a target nucleic acid in one or more biological samples, comprising the following steps:
   a) providing a multi-well plate, wherein each well of said multi-well plate consists of a single compartment, and wherein one or more wells of said multi-well plate contain:
      i) an absorbent matrix;
      ii) a biological sample on said absorbent matrix, wherein said biological sample comprises said target nucleic acid, and wherein said nucleic acid has not been extracted, washed, and/or eluted from said biological sample;
      iii) a reagent mixture for amplifying said nucleic acid; and
      iv) a reagent mixture for detecting the amplified nucleic acid;
   b) sealing said one or more wells of said multi-well plate;
   c) releasing said nucleic acid from said absorbent matrix;
   d) amplifying said nucleic acid; and
   e) detecting the amplified nucleic acid through the use of a labelled probe as a result of fluorescence resonance energy transfer; wherein:
      steps c) through e) are performed in said one or more wells of said multi-well plate without removing said absorbent matrix from said one or more wells of said multi-well plate and without opening said one or more wells of said multi-well plate.

15. The method according to claim 14, wherein said biological material is applied to said absorbent matrix prior to transferring said absorbent matrix and said biological sample to said one or more wells of said multi-well plate.

16. The method according to claim 15, wherein said biological sample is applied to said absorbent matrix immediately prior to transferring said absorbent matrix and said biological sample to one or more wells of said multi-well plate, without drying or storage.

17. The method according to claim 14, wherein said absorbent matrix is transferred to said one or more wells of said multi-well plate prior to application of said biological sample to said absorbent matrix.

18. The method according to claim 14, wherein said absorbent matrix comprises an absorbent material that does not irreversibly bind nucleic acids.

19. The method according to claim 18, wherein said absorbent matrix comprises one or more of a protein binding agent and a protein denaturing agent.

20. The method according to claim 18, wherein said absorbent matrix comprises a chaotropic agent.

21. The method according to claim 14, wherein in step a) at least part of said reagent mixture for amplifying nucleic acids and said reagent mixture for detecting amplified nucleic acids are contained in said one or more wells of said multi-well plate in dried form.

22. The method according to claim 14, wherein step d) is performed by polymerase chain reaction (PCR).

23. The method according to claim 14, wherein step e) is performed by hybridizing said amplified nucleic acid to a fluorescently labelled probe.

24. The method according to claim 21, further comprising adding water to said one or more wells of said multi-well plate prior to step b).

25. The method according to claim 14, wherein said target nucleic acid is DNA.

26. The method according to claim 14, wherein said target nucleic acid is RNA.

27. The method according to claim 1, wherein said biological sample is blood.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
aagcacagtg gaagaatttc                                              20

<210> SEQ ID NO 2
<211> LENGTH: 19
<212> TYPE: DNA
```

```
<213> ORGANISM: Artificial Sequence
<220> FEATURE:
<223> OTHER INFORMATION: Primer

<400> SEQUENCE: 2
ctcttctagt tggcatgct                                              19

<210> SEQ ID NO 3
<211> LENGTH: 33
<212> TYPE: DNA
<213> ORGANISM: Artificial Sequence
<220> FEATURE:
<223> OTHER INFORMATION: Probe

<400> SEQUENCE: 3
taaagaaaat atcatctttg gtgtttccta taa                              33

<210> SEQ ID NO 4
<211> LENGTH: 15
<212> TYPE: DNA
<213> ORGANISM: Artificial Sequence
<220> FEATURE:
<223> OTHER INFORMATION: Probe

<400> SEQUENCE: 4
atgatatttt cttta                                                  15

<210> SEQ ID NO 5
<211> LENGTH: 19
<212> TYPE: DNA
<213> ORGANISM: Artificial Sequence
<220> FEATURE:
<223> OTHER INFORMATION: Probe

<400> SEQUENCE: 5
accaaagatg atatttaaa                                              19

<210> SEQ ID NO 6
<211> LENGTH: 12
<212> TYPE: DNA
<213> ORGANISM: Artificial Sequence
<220> FEATURE:
<223> OTHER INFORMATION: Probe

<400> SEQUENCE: 6
tcattggtgt tt                                                     12
```